United States Patent
Izumi et al.

(10) Patent No.: US 9,987,206 B2
(45) Date of Patent: Jun. 5, 2018

(54) COSMETIC PRODUCT FOR HAIR DECOLORING OR HAIR COLORING

(71) Applicant: KAO CORPORATION, Tokyo (JP)

(72) Inventors: Keiko Izumi, Sendai (JP); Toshio Ogawa, Bunkyo-ku (JP); Kumiko Kamitakahara, Koto-ku (JP)

(73) Assignee: KAO CORPORATION, Tokyo (JP)

( * ) Notice: Subject to any disclaimer, the term of this patent is extended or adjusted under 35 U.S.C. 154(b) by 0 days. days.

(21) Appl. No.: 14/909,010

(22) PCT Filed: Jul. 30, 2014

(86) PCT No.: PCT/JP2014/070115
§ 371 (c)(1),
(2) Date: Jan. 29, 2016

(87) PCT Pub. No.: WO2015/016280
PCT Pub. Date: Feb. 5, 2015

(65) Prior Publication Data
US 2016/0166484 A1 Jun. 16, 2016

(30) Foreign Application Priority Data
Jul. 31, 2013 (JP) ................ 2013-159156

(51) Int. Cl.
| | | |
|---|---|---|
| A61K 8/34 | (2006.01) | |
| A61Q 5/08 | (2006.01) | |
| A61Q 5/10 | (2006.01) | |
| A61K 8/04 | (2006.01) | |
| A61K 8/22 | (2006.01) | |
| A61K 8/41 | (2006.01) | |
| A61K 8/86 | (2006.01) | |

(52) U.S. Cl.
CPC ............ *A61K 8/342* (2013.01); *A61K 8/046* (2013.01); *A61K 8/22* (2013.01); *A61K 8/416* (2013.01); *A61K 8/86* (2013.01); *A61Q 5/08* (2013.01); *A61Q 5/10* (2013.01); *A61K 2800/4324* (2013.01); *A61K 2800/48* (2013.01); *A61K 2800/592* (2013.01); *A61K 2800/5922* (2013.01); *A61K 2800/87* (2013.01); *A61K 2800/882* (2013.01)

(58) Field of Classification Search
CPC ...... A61K 8/046; A61K 2800/88; A61K 8/19; A61K 8/22; A61K 8/415; A61K 2800/4324; A61K 2800/87; A61K 2800/882; A61K 8/342; A61K 8/345; A61K 8/347; A61K 8/411; A61K 8/42; A61K 8/442; A61K 8/463; A61Q 5/10; A61Q 5/08

See application file for complete search history.

(56) References Cited

U.S. PATENT DOCUMENTS

| | | |
|---|---|---|
| 2004/0213752 A1 | 10/2004 | Fujinuma et al. |
| 2010/0251488 A1 | 10/2010 | Fujinuma et al. |
| 2011/0277782 A1 | 11/2011 | Iijima et al. |
| 2012/0305021 A1 | 12/2012 | Iijima et al. |
| 2013/0125918 A1 | 5/2013 | Nobuto et al. |

FOREIGN PATENT DOCUMENTS

| | | | |
|---|---|---|---|
| CN | 1541642 A | 11/2004 | |
| CN | 103079532 A | 5/2013 | |
| EP | 2 407 149 A1 | 1/2012 | |
| JP | 2003-252735 A | 9/2003 | |
| JP | 2004-339216 A | 12/2004 | |
| JP | 2007-291015 A | 11/2007 | |
| JP | 2008-137934 A | 6/2008 | |
| JP | 2008-137935 A | 6/2008 | |
| JP | 2008-290949 A | 12/2008 | |
| JP | 2008290949 A * | 12/2008 | ............... A61K 8/34 |
| JP | 2013-60391 A | 4/2013 | |
| JP | 2013060291 A * | 4/2013 | ............... A61K 8/97 |
| WO | WO 2012/060239 A1 | 5/2012 | |

OTHER PUBLICATIONS

International Search Report dated Oct. 7, 2014 in PCT/JP14/70115 Filed Jul. 30, 2014.
Extended Search Report dated Dec. 12, 2016 in European Patent Application No. 14831860.3.

* cited by examiner

*Primary Examiner* — Audrea Buckley
(74) *Attorney, Agent, or Firm* — Oblon, McClelland, Maier & Neustadt, L.L.P.

(57) ABSTRACT

A cosmetic product for hair bleaching or hair dyeing, which comprises a first part containing an alkali agent, a second part containing hydrogen peroxide, and a non-aerosol foamer container for discharging a mixed solution containing the first part and the second part in the form of foam, wherein the cosmetic product for hair bleaching or hair dyeing contains the following component (A) in the second part:

(A) saturated aliphatic alcohols containing the following components (A1) and (A2):

$$R^1\text{—OH} \quad (A1)$$

$$R^2\text{—OH} \quad (A2)$$

wherein $R^1$ represents a $C_{12-18}$ linear chain alkyl group, and $R^2$ represents a $C_{19-24}$ linear chain alkyl group.

17 Claims, No Drawings

COSMETIC PRODUCT FOR HAIR DECOLORING OR HAIR COLORING

FIELD OF THE INVENTION

The present invention relates to a cosmetic product for hair bleaching or hair dyeing.

BACKGROUND OF THE INVENTION

Conventionally, as two-part hair bleaches or hair dyes, those in a liquid or cream form have been broadly used from old times. However, it is difficult for unskilled persons to apply these liquid or cream agents to hair without causing unevenness. The viscosity of a mixture to be applied to hair is adjusted to a high value which is approximately 1000 to 10000 mPa·s, so that an agent is prevented from dripping down while it is left for a certain time of period, and thus, it is difficult to uniformly spread the agent, and it is also difficult to allow the agent to sufficiently penetrate into the root of hair. Moreover, in order to apply the agent to the root portion of hair and to the back of the head, skills such as blocking (segmentation of hair) and a two-mirror technique for confirming application of the agent to the hair are required, and a lot of time is also required.

In contrast to such a two-part hair bleach or two-part hair dye, a mixed solution of two-part hair bleaches or two-part hair dyes, which is discharged from a non-aerosol foamer container in the form of foam, has been known (Patent Document 1). In the case of this hair bleach or hair dye, since a mixed solution of a first part and a second part is discharged from a non-aerosol foamer container in the form of foam, even an unskilled person can easily apply the agent to hair without causing unevenness, and color unevenness does not occur at the time of finishing. Since this agent can be easily applied to hair, skills such as blocking and a two-mirror technique are not necessary, and the time required for hair dye is significantly shorter than that in the case of the conventional agent. Hence, since a mixed solution of two-part hair agents has performance much more excellent than the conventional hair agent, it has been supported by a wide range of customers, regardless of sex and age. As such, various products have been developed for the needs of a wide variety of customers.

Moreover, Patent Document 2 discloses a technique of setting a ratio between a surfactant and a higher alcohol mixed into a two-part hair bleach or a two-part hair dye at a specific ratio and thereby improving foaming properties at a low temperature.

(Patent Document 1) JP-A-2004-339216
(Patent Document 2) JP-A-2007-291015

SUMMARY OF THE INVENTION

The present invention provides a cosmetic product for hair bleaching or hair dyeing, which comprises a first part containing an alkali agent, a second part containing hydrogen peroxide, and a non-aerosol foamer container for discharging a mixed solution containing the first part and the second part in the form of foam, wherein the cosmetic product for hair bleaching or hair dyeing contains the following component (A) in the second part:

(A) saturated aliphatic alcohols containing the following components (A1) and (A2):

a saturated aliphatic alcohol represented by $R^1$—OH (A1)

wherein represents a $C_{12\text{-}18}$ linear chain alkyl group, and a saturated aliphatic alcohol represented by $R^2$—OH (A2)

wherein $R^2$ represents a $C_{19\text{-}24}$ linear chain alkyl group.

DETAILED DESCRIPTION OF THE INVENTION

In order to make foam using a non-aerosol foamer container, the viscosity of a mixed solution needs to be lowered. On the other hand, it is also required that a mixed solution applied to hair is prevented from dripping down. Paragraph [0026] of Patent Document 1 discloses a method of allowing a mixed solution to comprise a higher alcohol in order to suppress the dripping of the mixed solution. However, this method has been problematic in that, if a higher alcohol is used, the viscosity of the mixed solution increases, for example, when the liquid temperature decreases during the winter season, and in that foam is hardly discharged from a foamer container, and thereby, a good foam product cannot be obtained.

Moreover, the technique described in Patent Document 2 has also been problematic in that when a two-part hair bleach or hair dye is preserved for a long period of time, a mixed solution is thickened under a low temperature environment, and foam is hardly discharged from a foamer container, and further, the discharged foam has a rough texture. It is considered that this is caused by a phenomenon that the diameter of an emulsified particle contained in a second part becomes large as the time has passed. It has been found that, even if the amount of higher alcohol is reduced to improve foam dischargeability in order to improve foam dischargeability, a foam product discharged from a foamer container is still easily destroyed when the liquid temperature increases, for example, in the summer season.

The present invention relates to a cosmetic product for hair bleaching or hair dyeing, in which foam can be easily discharged from a foamer container either at a low temperature or at a high temperature, or even when it is preserved for a long period of time, and further in which a good foam product can be stably obtained.

The present inventors have found that a cosmetic product for hair bleaching or hair dyeing, which is used by being discharged from a non-aerosol foamer container in the form of foam, is allowed to comprise a combination of specific higher alcohols in a mixture containing a first part and a second part, so that the obtained cosmetic product satisfies the aforementioned requirements.

The cosmetic product for hair bleaching or hair dyeing of the present invention can be used as a two-part cosmetic product in which a first part and a second part are mixed and used, or as a three-part cosmetic product in which a third part which is, for example, a granulated substance such as a persulfate is mixed with the first part and the second part and is used. In the present invention, the mixture means a mixture of a first part and a second part in the case of a two-part cosmetic product, and a mixture of a first part, a second part and a third part in the case of a three-part cosmetic product.

[Alkali Agent]

The first part contains an alkali agent. Examples of the alkali agent include: ammonia and a salt thereof; alkanolamines such as monoethanolamine, isopropanolamine, 2-amino-2-methylpropanol and 2-aminobutanol, and salts thereof; alkanediamines such as 1,3-propanediamine, and salts thereof; and carbonates such as guanidine carbonate, sodium carbonate, potassium carbonate, sodium hydrogen carbonate, and potassium hydrogen carbonate. These alkali agents may be used in combination of two or more agents. In terms of a sufficient hair dye effect, the content of the alkali agent in the mixture is preferably 0.05% by mass or more, more preferably 0.1% by mass or more, and even more preferably 0.2% by mass or more. In addition, in terms of a reduction in hair damage or scalp irritation, it is preferably 15% by mass or less, more preferably 10% by mass or less, and even more preferably 5% by mass or less.

[Hydrogen Peroxide]

The second part contains hydrogen peroxide. The content of hydrogen peroxide in the second part is preferably 1% by mass or more, and more preferably 3% by mass or more. In addition, it is preferably 9% by mass or less, and more preferably 6% by mass or less. The content of the hydrogen peroxide in the mixture is preferably 1% by mass or more, and more preferably 2% by mass or more. In addition, it is preferably 6% by mass or less, and more preferably 5% by mass or less. Furthermore, from the viewpoint of suppression of the decomposition of the hydrogen peroxide, the pH of the second part is preferably 2 or more, and more preferably 2.5 or more. In addition, it is preferably 6 or less, and more preferably 4 or less.

[Component (A): Saturated Aliphatic Alcohol]

The cosmetic product for hair bleaching or hair dyeing of the present invention contains the following saturated aliphatic alcohols as a component (A) in the second part:

(A) saturated aliphatic alcohols containing the following components (A1) and (A2):

a saturated aliphatic alcohol represented by $R^1$—OH (A1)

wherein $R^1$ represents a $C_{12\text{-}18}$ linear chain alkyl group, and a saturated aliphatic alcohol represented by $R^2$—OH (A2)

wherein $R^2$ represents a $C_{19\text{-}24}$ linear chain alkyl group.

<Component (A1)>

$R^1$ in the formula of the component (A1) preferably contains 14 to 18 carbon atoms, from the viewpoint of foam stability under high temperature conditions.

From the viewpoint of foam stability under high temperature conditions, the content of the component (A1) in the second part is preferably 0.01% by mass or more, more preferably 0.03% by mass or more, and even more preferably 0.05% by mass or more. In addition, it is preferably 15% by mass or less, more preferably 10% by mass or less, even more preferably 5% by mass or less, further preferably 3% by mass or less, still further preferably 2% by mass or less, still further preferably 1.5% by mass or less, and still further preferably 1% by mass or less.

<Component (A2)>

$R^2$ in the formula of the component (A2) preferably contains 20 or more and 24 or less carbon atoms, from the viewpoint of foam dischargeability under low temperature conditions.

From the viewpoint of foam dischargeability under low temperature conditions, the content of the component (A2) in the second part is preferably 0.01% by mass or more, more preferably 0.03% by mass or more, and even more preferably 0.05% by mass or more. In addition, it is preferably 15% by mass or less, more preferably 10% by mass or less, even more preferably 5% by mass or less, further preferably 3% by mass or less, still further preferably 2% by mass or less, still further preferably 1.5% by mass or less, and still further preferably 1% by mass or less.

From the viewpoint of foam dischargeability under low temperature conditions and foam stability under high temperature conditions, the total content of the components (A1) and (A2) in the second agent is preferably 0.02% by mass or more, more preferably 0.06% by mass or more, and even more preferably 0.1% by mass or more. In addition, it is preferably 15% by mass or less, more preferably 10% by mass or less, even more preferably 5% by mass or less, further preferably 3% by mass or less, still further preferably 2% by mass or less, and still further preferably 1.5% by mass or less.

From the viewpoint of foam dischargeability under low temperature conditions and foam stability under high temperature conditions, the mass ratio between the components (A1) and (A2), ((A1):(A2)), in the second part is preferably 10:1 to 1:20, more preferably 5:1 to 1:10, and even more preferably 3:1 to 1:7.

[Component (B): Ionic Surfactant]

The second part of the cosmetic product for hair bleaching or hair dyeing of the present invention preferably contains an ionic surfactant. Examples of the ionic surfactant include a cationic surfactant, an anionic surfactant, and an amphoteric surfactant.

<Cationic Surfactant>

The cationic surfactant is preferably (B1) a mono-long-chain-alkylammonium salt represented by the following formula (1):

wherein $R^3$ represents a $C_{12\text{-}24}$ linear chain alkyl group.

$R^3$ in the formula (1) preferably contains 12 to 18 carbon atoms, from the viewpoint of foam stability under high temperature conditions.

A more preferred cationic surfactant can be a combination of (B2) a mono-long-chain-alkylammonium salt represented by the following formula (2) and (B3) a mono-long-chain-alkylammonium salt represented by the following formula (3):

wherein $R^4$ represents a $C_{12\text{-}16}$ linear chain alkyl group.

wherein $R^5$ represents a $C_{18\text{-}24}$ linear chain alkyl group.

$R^4$ in the formula (2) preferably contains 14 to 16 carbon atoms, from the viewpoint of foam stability under high temperature conditions.

From the viewpoint of foam stability under high temperature conditions, the content of the component (B2) in the second part is preferably 0.01% by mass or more, more preferably 0.02% by mass or more, even more preferably 0.03% by mass or more. In addition, it is preferably 10% by mass or less, more preferably 5% by mass or less, even more preferably 3% by mass or less, further preferably 2% by mass or less, and still further preferably 1% by mass or less.

$R^5$ in the formula (3) contains preferably 18 to 22 carbon atoms, and more preferably 18 to 20 carbon atoms, from the viewpoint of foam stability under high temperature conditions.

From the viewpoint of foam stability under high temperature conditions, the content of the component (B3) in the second part is preferably 0.01% by mass or more, more preferably 0.02% by mass or more, and even more preferably 0.03% by mass or more. In addition, it is preferably 10% by mass or less, more preferably 5% by mass or less, even more preferably 3% by mass or less, further preferably 2% by mass or less, and still further preferably 1% by mass or less.

From the viewpoint of foam dischargeability under low temperature conditions and foam stability under high temperature conditions, the mass ratio of the component (B2) to the component (B3), ((B2)/(B3)), in the second part is preferably 20 to 0.05, more preferably 10 to 0.1, even more preferably 8 to 0.5, and further preferably 5 to 1.

<Anionic Surfactant>

Examples of the anionic surfactant include: sulfate anionic surfactants such as alkyl sulfate and alkyl ether sulfate; carboxylate anionic surfactants such as N-acylamino acid salt, N-acyl-N-alkylamino acid salt, amide-type N-acylamino acid salt, ether carboxylate, fatty acid salt, and the salt of alkyl succinate or alkenyl succinate; sulfonate anionic surfactants such as sulfosuccinate, isethionate, taurine salt, alkylbenzene sulfonate, α-olefin sulfonate, and alkane sulfonate anionic surfactants; and phosphate anionic surfactants such as alkyl phosphate and alkyl ether phosphate. Among these anionic surfactants, carboxylate and sulfate anionic surfactants are preferable, and among them, carboxylate anionic surfactants are more preferable. Among the carboxylate anionic surfactants, N-acylamino acid salt and ether carboxylate are preferable. Further, among these, N-acyl glutamate having an acyl group containing 10 to 18, preferably 10 to 16 and more preferably 10 to 14 carbon atoms, and polyoxyethylene alkyl carboxylate that has an alkyl group containing 10 to 18, preferably 10 to 16 and more preferably 10 to 14 carbon atoms and has an oxyethylene group having the average number of moles added which is 3 to 15, preferably 3 to 12 and more preferably 4 to 10, are preferable.

<Amphoteric Surfactant>

Examples of the amphoteric surfactant include carbobetaine, amidobetaine, sulfobetaine, hydroxysulfobetaine, amidosulfobetaine, phosphobetaine, and imidazolinium surfactants, which have an alkyl group, an alkenyl group, or an acyl group containing 8 to 24 carbon atoms. Among these surfactants, carbobetaine surfactants and sulfobetaine surfactants are preferable. Examples of the preferred amphoteric surfactant include lauric acid amidopropylbetaine, coconut oil fatty acid amidopropylbetaine, lauryldimethylaminoacetic acid betaine, and lauryl hydroxy sulfobetaine.

From the viewpoint of foam dischargeability under low temperature conditions and foam stability under high temperature conditions, the total content of the component (B) in the second part is preferably 0.02% by mass or more, more preferably 0.04% by mass or more, and even more preferably 0.06% by mass or more. In addition, it is preferably 20% by mass or less, more preferably 15% by mass or less, even more preferably 10% by mass or less, further preferably 5% by mass or less, still further preferably 3% by mass or less, still further preferably 2% by mass or less, and still further preferably 1.5% by mass or less.

From the viewpoint of foam dischargeability under low temperature conditions and foam stability under high temperature conditions, the mass ratio of the component (B) to the total amount of the components (A1) and (A2), ((B)/[(A1)+(A2)]), in the second part is preferably 10 to 0.05, more preferably 8 to 0.15, even more preferably 6 to 0.25, and further preferably 3 to 0.3.

[Component (C): Polyoxyethylene Alkyl Ether]

From the viewpoint of foam dischargeability under low temperature conditions, the second part of the cosmetic product for hair bleaching or hair dyeing of the present invention contains a polyoxyethylene alkyl ether represented by the following formula as a component (C):

$$R^6-O-(CH_2CH_2O)_n-H \quad (C)$$

wherein $R^6$ represents a $C_{10-24}$ linear or branched chain alkyl group, and n represents the average number of moles added which is 50 to 210.

From the viewpoint of foam dischargeability under low temperature conditions, $R^6$ in the formula of the component (C) contains preferably 12 to 24 carbon atoms, and more preferably 14 to 22 carbon atoms. In addition, $R^6$ is preferably a linear chain alkyl group.

From the viewpoint of foam dischargeability under low temperature conditions, n in the formula of the component (C) is preferably 60 or more, more preferably 80 or more, and even more preferably 100 or more. In addition, it is preferably 200 or less.

From the viewpoint of foam dischargeability under low temperature conditions, the content of the component (C) in the second part is preferably 0.01% by mass or more, more preferably 0.03% by mass or more, and even more preferably 0.05% by mass or more. In addition, it is preferably 15% by mass or less, more preferably 10% by mass or less, even more preferably 5% by mass or less, further preferably 3% by mass or less, still further preferably 2% by mass or less, and still further preferably 1.5% by mass or less.

[Dye]

When the cosmetic product for hair bleaching or hair dyeing of the present invention is a cosmetic product for hair dyeing, it may comprise an oxidation dye intermediate or a direct dye in the first part.

<Oxidation Dye Intermediate>

As an oxidation dye intermediate, a known precursor and a known coupler, which are generally used in hair dyes, can be used. Examples of the precursor include p-phenylenediamine, toluene-2,5-diamine, N-phenyl p-phenylenediamine, N,N-bis(hydroxyethyl) p-phenylenediamine, 2-hydroxyethyl p-phenylenediamine, p-aminophenol, p-methylaminophenol, 4-amino-m-cresol, ortho-aminophenol, and salts thereof.

Examples of the coupler include resorcin, 2-methylresorcin, naphthol, 1,5-dihydroxynaphthalene, 5-amino-ortho-cresol, m-phenylenediamine, m-aminophenol, 2,4-diaminophenoxyethanol, 2,6-diaminopyridine, 2-methyl-5-hydroxyethylaminophenol, 2-amino-3-hydroxypyridine, and salts thereof.

Two or more precursors, or two or more couplers may be used in combination. The content of each of the precursor and the coupler in the first part is preferably 0.01% by mass or more, and more preferably 0.1% by mass or more. In addition, it is preferably 5% by mass or less, and more preferably 4% by mass or less.

<Direct Dye>

Examples of the direct dye include an acidic dye, a nitro dye, a disperse dye, and a basic dye. More specifically, examples of the acidic dye include Blue No. 1, Violet No. 401, Black No. 401, Orange No. 205, Red No. 227, Red No. 106, Yellow No. 203, and Acidic Orange 3. Examples of the nitro dye include 2-nitro-p-phenylenediamine, 2-amino-6-chloro-4-nitrophenol, 3-nitro-p-hydroxyethylaminophenol, 4-nitro-o-phenylenediamine, 4-amino-3-nitrophenol, 4-hydroxypropylamino-3-nitrophenol, HC Blue 2, HC Orange 1, HC Red 1, HC yellow 2, HC Yellow 4, HC Yellow 5, HC Red 3, and N,N-bis(2-hydroxyethyl)-2-nitro-p-phenylenediamine. Examples of the disperse dye include Disperse Violet 1, Disperse Blue 1, and Disperse Black 9. Examples of the basic dye include Basic Blue 99, Basic Brown 16, Basic Brown 17, Basic Red 76, Basic Yellow 76, Basic Orange 31, and Basic Red 51.

Two or more direct dyes may be used in combination, and the direct dye may also be used in combination with an oxidation dye intermediate. The content of the direct dye in the first part is preferably 0.001% by mass or more, and more preferably 0.01% by mass or more. In addition, it is preferably 5% by mass or less, and more preferably 3% by mass or less.

[Nonionic Surfactants Other than Component (C)]

The cosmetic product for hair bleaching or hair dyeing of the present invention may contain a nonionic surfactant other than the component (C) in the second part.

Examples of such a nonionic surfactant other than the component (C) include alkyl polyglucoside and alkyl glyceryl ether. As such alkyl polyglucoside, alkyl polyglucoside, which has an alkyl group containing preferably 8 to 18, more preferably 8 to 14, and even more preferably 9 to 11 carbon atoms, is preferable, and further, this alkyl group is preferably a linear chain alkyl group. The average degree of polymerization of glucoside is preferably 1 to 5, and more preferably 1 to 2. As such alkyl glyceryl ether, alkyl glyceryl ether, which has an alkyl group containing preferably 8 to 18, and more preferably 8 to 12 carbon atoms, is preferable, and this alkyl group is preferably a branched chain alkyl group.

Two or more nonionic surfactants other than the component (C) may also be used in combination. From the viewpoint of the stability of each agent, the content of such a nonionic surfactant other than the component (C) in the mixture is preferably 2% by mass or more, more preferably 2.5% by mass or more, and even more preferably 3% by mass or more. In addition, it is preferably 20% by mass or less, more preferably 15% by mass or less, even more preferably 10% by mass or less, further preferably 8% by mass or less, still further preferably 7% by mass or less, and still further preferably 6%, by mass or less.

[Polyhydric Alcohol]

The cosmetic product for hair bleaching or hair dyeing of the present invention may further contain a polyhydric alcohol in at least one of the parts. An example is a polyhydric alcohol containing 2 to 20 carbon atoms. Specific examples of such polyhydric alcohol include: alkylene glycols such as ethylene glycol, diethylene glycol, triethylene glycol, polyethylene glycol, propylene glycol, dipropylene glycol, polypropylene glycol, 1,2-butylene glycol, 1,3-butylene glycol, pentylene glycol, and hexylene glycol; glycerins such as glycerin, diglycerin, and polyglycerin; sugar alcohols such as xylitol, mannitol, galactitol, and sorbit; and other polyhydric alcohols such as trimethylolethane, trimethylolpropane, and pentaerythritol.

Two or more polyhydric alcohols may be used in combination. Moreover, in terms of the achievement of the excellent effect of giving moisture to hair and suppressing hair dryness, the content of the polyhydric alcohol in the mixture is preferably 0.1% by mass or more, more preferably 0.5% by mass or more, and even more preferably 1% by mass or more. In addition, it is preferably 20% by mass or less, more preferably 15% by mass or less, even more preferably 10% by mass or less, and further preferably 5% by mass or less.

[Solvent]

For the cosmetic product for hair bleaching or hair dyeing of the present invention, water, and as necessary, an organic solvent can be used as a solvent. Examples of the organic solvent include aromatic alcohols such as benzyl alcohol and 2-benzyloxyethanol, lower alkanols such as ethanol and 2-propanol, polyols such as propylene glycol, 1,3-butanediol, diethylene glycol and glycerin, cellosolves such as ethyl cellosolve, butyl cellosolve and benzyl cellosolve, and carbitols such as ethyl carbitol and butyl carbitol.

[Other Optional Components]

In addition to the above described components, other components, which are generally used as raw materials for cosmetic products, can be added to the cosmetic product for hair bleaching or hair dyeing of the present invention. Examples of such optional components include hydrocarbons, animal and vegetable oils and fats, higher fatty acids, natural or synthetic polymers, silicones, ethers, protein derivatives, hydrolyzed proteins, amino acids, antiseptics, chelating agents, stabilizers, antioxidants, plant extracts, herbal extracts, vitamins, perfumes, and ultraviolet absorbers.

[Maximum Diameter of Emulsified Particle in Second Part]

From the viewpoint of foam dischargeability under low temperature conditions and foam stability under high temperature conditions, the maximum diameter of the emulsified particle in the second part of the cosmetic product for hair bleaching or hair dyeing of the present invention, immediately after the production thereof, is preferably 2.5 μm or less, more preferably 2.0 μm or less, even more preferably 1.5 μm or less, further preferably 1.2 μm or less, still further preferably 1.0 μm or less, and still further preferably 0.9 μm or less.

Moreover, from the viewpoint of foam dischargeability under low temperature conditions, which are immediately after the production of the product and after long-term preservation thereof, an increase in the maximum diameter of the emulsified particle from immediately after the production of the product to after long-term preservation thereof is preferably 3.0 μm or less, more preferably 2.0 μm or less, even more preferably 1.0 μm or less, and further preferably 0.9 μm or less.

By setting the maximum diameter of the emulsified particle in the second part within the aforementioned range, foam stability can be ensured, while keeping the mixed solution at a low viscosity in all of temperature zones, without depending on the composition of the first part. Thus, a good foam product can be discharged from a foamer container stably, either at a low temperature or at a high temperature.

Herein, with regard to the measurement of the diameter of the emulsified particle in the second part, employing DYNAMIC LIGHT SCATTERING PARTICLE SIZE ANALYZER LB-500 manufactured by HORIBA, "Organic sample" (refractive index: 1.600-0.000 i) was selected as a sample, and "Water" (refractive index: 1.333) was selected as a dispersion medium, and thereafter, a volume distribution of the diameters of the emulsified particles in the second part was measured.

[pH]

In the cosmetic product for hair bleaching or hair dyeing of the present invention, the pH (25° C.) of the mixture is preferably 8 or more and more preferably 9 or more, and also, it is preferably 12 or less, more preferably 11 or less and even more preferably 10.5 or less, in terms of hair dye effect and skin irritation. Examples of a pH adjuster include: the above described alkali agents; inorganic acids such as hydrochloric acid and phosphoric acid; organic acids such as citric acid, glycolic acid, and lactic acid; and phosphates such as potassium dihydrogen phosphate and disodium hydrogen phosphate.

[Viscosity]

In the cosmetic product for hair bleaching or hair dyeing of the present invention, the range of the viscosity of the mixture is preferably 1 mPa·s or more, more preferably 2 mPa·s or more, even more preferably 3 mPa·s or more, and further preferably 5 mPa·s or more. In addition, it is preferably 800 mPa·s or less, more preferably 500 mPa·s or less, even more preferably 400 mPa·s or less, further preferably 300 mPa·s or less, and still further preferably 200 mPa·s or less. It is to be noted that the viscosity is herein measured at 5° C., employing a type-B rotary viscometer (model; digital viscometer TV-10, TOKI SANGYO CO., LTD.), using rotor No. 1, and at a rotation rate of 60 rpm when the measurement target has a viscosity of 100 mPa·s or less, or at a rotation rate of 30 rpm when it has a viscosity of 100 to 200 mPa·s, or at a rotation rate of 12 rpm when it has a viscosity of 200 mPa·s or more. The measurement is carried out from a measurement with the highest rotation number in descending order. The measurement is terminated at a time point at which the measurement could be carried out without going off the scale, and the subsequent measurements each having a smaller rotation number are not carried out. It is to be noted that the viscosity of the mixed solution should be measured three minutes after initiation of the mixing of individual parts.

[Foamer Container]

In the present invention, the foamer container is a non-aerosol container, and is used to mix a mixture containing a first part and a second part with air without using a propellant, and to discharge the obtained mixture in the form of foam. Using this foamer container, the effect of preventing the scattering of the discharged agent, and the effect of discharging foam, in which the first part is uniformly mixed with the second part, can be obtained. In particular, in comparison to an aerosol container, a non-aerosol container enables inexpensive production of products. Moreover, since such a non-aerosol container does not need a high-pressure gas propellant, the obtained products can be managed more safely during distribution.

As a foamer container, a known pump foamer container having a foam discharging means, a squeeze foamer container, a motorized foamer, a pressure accumulator pump foamer container, and the like can be used. More specific examples include pump foamers type-E3 and type-F2 described in *Shokuhin to Yoki* (Vol. 35, No. 10, pp. 588 to 593 (1994); Vol. 35, No. 11, pp. 624 to 627 (1994); Vol. 36, No. 3, pp. 154 to 158 (1995)) (both of which are manufactured by DAIWA CAN COMPANY), Squeeze Foamer (DAIWA CAN COMPANY), Motorized Foamer (Matsushita Electric Works, Ltd.), and Air Spray Foamer (Air Spray International, Inc.). As foamer containers used for the two-part hair dye of the present invention, a pump foamer container and a squeeze foamer container are preferable because these containers are inexpensive and are easy to be handled.

Such a pump foamer container or a squeeze foamer container has a foam generation portion such as a net. From the viewpoint that when a mixture containing a first part and a second part is dried and solidified and is thereby clogged, such a solidified product is immediately dissolved by the flow of foam at the subsequent discharge, so that such clogging can be solved, it is preferable for the pump foamer container or the squeeze foamer container to have a thin net. In this case, the mesh constituting the net is preferably 50 to 280 meshes, more preferably 90 to 250 meshes, and even more preferably 130 to 220 meshes. Herein, the mesh indicates the number of squares per inch. Using a net constituted with this range of meshes, creamy foam can be generated. Moreover, preferred examples of a material for such mesh include nylon and polyester.

In the cosmetic product for hair bleaching or hair dyeing of the present invention, the used foamer container comprises at least one of such net, and preferably a plurality of such nets, and particularly, from the viewpoint of economic efficiency and foam stability, it is preferable to use two nets for the foamer container.

In such a foamer container, a portion that is allowed to come into contact with a content (i.e., an inner wall of the container, an inner wall of a foam discharging means, etc.) is preferably constituted with a material, which is not eroded by alkali and hydrogen peroxide and through which oxygen generated as a result of the decomposition of hydrogen peroxide permeates.

When the cosmetic product for hair bleaching or hair dyeing of the present invention is used as a two-part product, a first part and a second part may be filled into different containers, separately, wherein these containers differ from a foamer container, and the two parts may be transferred into the foamer container upon application, and may be then mixed with each other. Alternatively, one part may be filled into a foamer container, the other part may be filled into another container, and the other part may be transferred into the foamer container upon application. In this case, in order to prevent an increase in the pressure in the container due to oxygen generated as a result of the decomposition of hydrogen peroxide, the second part is preferably filled into a gas-permeable container, and in particular, a foamer container consisting of an oxygen permeable material (e.g. polyethylene). On the other hand, a hardly oxygen-permeable container is preferably used for the first part, in order to prevent an oxidation dye from oxidation.

The mixing ratio between the first part and the second part in the cosmetic product for hair bleaching or hair dyeing of the present invention is preferably 1:4 to 4:1, and more preferably 1:2 to 1:1, at a mass ratio.

[Gas-Liquid Mixing Ratio]

From the viewpoint of the compatibility of the agent with hair and easy application to hair, the gas-liquid mixing ratio between air and the mixture, which is caused by the foam discharging means of the foamer container, is preferably 5 to 40 mL/g, and more preferably 8 to 30 mL/g. It is to be noted that the gas-liquid mixing ratio used herein is a value measured as follows.

First, the gas-liquid mixing ratio is obtained by measuring the mass and volume of foam that has been discharged at 25° C. 100 g of a mixture is placed in a squeeze foamer container (DAIWA CAN COMPANY, volume: 210 mL, mesh roughness (mesh opening): 150 meshes in a mixing chamber (150 squares per inch (25.4 mm)) and 200 meshes at a tip), and at a time point at which the balance has become 80 g, 20 g of foam is discharged to a 1000-mL measuring cylinder, and the volume of the foam is measured 1 minute after initiation of the discharge. The volume (mL) of the discharged foam is divided by 20 g of mass to obtain a gas-liquid mixing ratio (mL/g).

[How-To-Use]

In the cosmetic product for hair bleaching or hair dyeing of the present invention, in order to bleach or dye hair (particularly, hair of the head) using the mixture, it is preferable to comb hair in advance. Thereby, hair becomes hardly tangled during the after-mentioned re-foaming treatment, and thus, there is no risk of scattering the mixture. In addition, after hair has been combed, a blocking operation, which is commonly used in application of a bleaching agent or hair dye composition, does not need to be carried out, and further, it is preferable not to carry out such a blocking operation. Thereby, the after-mentioned operation of applying a bleaching agent or a hair dye composition to hair, or re-foaming operation, can be easily carried out. Subsequently, the first part of the cosmetic product for hair bleaching or hair dyeing of the present invention is mixed with the second part thereof in a foamer container. The foam agent discharged from the container may be directly applied to hair, or may also be applied to hair by hand or using a tool such as a brush. From the viewpoint of prevention of the scattering of the agent or the dripping of the liquid, it is more preferable to take the foam agent with a (gloved) hand, and then, to apply it to hair.

After application of the agent to hair, it is left for approximately 3 to 60 minutes, and preferably approximately 5 to 45 minutes. During this time, from the viewpoint of further preventing liquid from dripping down while it is left and sufficiently penetrating the mixture even into the root of hair, the agent is preferably foamed again on the hair. In order to foam the agent again, gas may be injected, or a tool such as a shaker or a brush may be used, or fingers may also be used. Among others, it is more preferable to use fingers.

The timing of foaming the agent again may be after the applied foam has completely disappeared, or may be in mid-course at which the applied foam is disappearing, or before the applied foam has changed. Otherwise, the timing of foaming the agent again may be after the foam has been applied to all of the ranges to which it intended to be applied, or may also be in mid-course of such application. Such re-foaming may be continuously carried out once, or may be intermittently repeated several times.

After completion of these operations, the mixture is washed away from the hair. Thereafter, shampoo or rinse is applied to the hair, as appropriate, and after that, the hair is washed with water and is then dried.

With regard to the aforementioned embodiments, hereinafter, the preferred aspects of the present invention will be further disclosed.

<1> A cosmetic product for hair bleaching or hair dyeing, which comprises a first part containing an alkali agent, a second part containing hydrogen peroxide, and a non-aerosol foamer container for discharging a mixed solution containing the first part and the second part in the form of foam, wherein the cosmetic product for hair bleaching or hair dyeing contains the following component (A) in the second part:

(A) saturated aliphatic alcohols containing the following components (A1) and (A2):

a saturated aliphatic alcohol represented by $R^1$—OH (A1)

wherein $R^1$ represents a $C_{12\text{-}18}$ linear chain alkyl group, and a saturated aliphatic alcohol represented by $R^2$—OH (A2)

wherein $R^2$ represents a $C_{19\text{-}24}$ linear chain alkyl group.

<2> The cosmetic product for hair bleaching or hair dyeing according to <1> above, wherein $R^1$ in the formula of the component (A1) preferably contains 14 to 18 carbon atoms.

<3> The cosmetic product for hair bleaching or hair dyeing according to <1> or <2> above, wherein the content of the component (A1) in the second part is preferably 0.01% by mass or more, more preferably 0.03% by mass or more, and even more preferably 0.05% by mass or more, and also, it is preferably 15% by mass or less, more preferably 10% by mass or less, even more preferably 5% by mass or less, further preferably 3% by mass or less, still further preferably 2% by mass or less, still further preferably 1.5% by mass or less, and still further preferably 1% by mass or less.

<4> The cosmetic product for hair bleaching or hair dyeing according to any one of <1> to <3> above, wherein $R^2$ in the formula of the component (A2) preferably contains 20 or more and 24 or less carbon atoms.

<5> The cosmetic product for hair bleaching or hair dyeing according to any one of <1> to <4> above, wherein the content of the component (A2) in the second part is preferably 0.01% by mass or more, more preferably 0.03% by mass or more, and even more preferably 0.05% by mass or more, and also, it is preferably 15% by mass or less, more preferably 10% by mass or less, even more preferably 5% by mass or less, further preferably 3% by mass or less, still further preferably 2% by mass or less, still further preferably 1.5% by mass or less, and still further preferably 1% by mass or less.

<6> The cosmetic product for hair bleaching or hair dyeing according to any one of <1> to <5> above, wherein the total content of the components (A1) and (A2) in the second agent is preferably 0.02% by mass or more, more preferably 0.06% by mass or more, and even more preferably 0.1% by mass or more, and also, it is preferably 15% by mass or less, more preferably 10% by mass or less, even more preferably 5% by mass or less, further preferably 3% by mass or less, still further preferably 2% by mass or less, and still further preferably 1.5% by mass or less.

<7> The cosmetic product for hair bleaching or hair dyeing according to any one of <1> to <6> above, wherein the mass ratio between the components (A1) and (A2), ((A1):(A2)), in the second part is preferably 10:1 to 1:20, more preferably 5:1 to 1:10, and even more preferably 3:1 to 1:7.

<8> The cosmetic product for hair bleaching or hair dyeing according to any one of <1> to <7> above, wherein the second part preferably further contains (B) an ionic surfactant.

<9> The cosmetic product for hair bleaching or hair dyeing according to <8> above, wherein the mass ratio of the component (B) to the total amount of the components (A1) and (A2), ((B)/[(A1)+(A2)]), in the second part is preferably 10 to 0.05, more preferably 8 to 0.15, even more preferably 6 to 0.25, and further preferably 3 to 0.3.

<10> The cosmetic product for hair bleaching or hair dyeing according to <8> or <9> above, wherein the component (B) preferably contains (B1) a mono-long-chain-alkylammonium salt represented by the following formula (1):

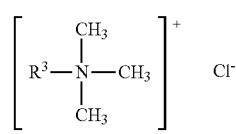

wherein R³ represents a $C_{12-24}$ linear chain alkyl group.

<11> The cosmetic product for hair bleaching or hair dyeing according to <8> or <9> above, wherein the component (B) preferably contains a combination of (B2) a mono-long-chain-alkylammonium salt represented by the following formula (2) and (B3) a mono-long-chain-alkylammonium salt represented by the following formula (3):

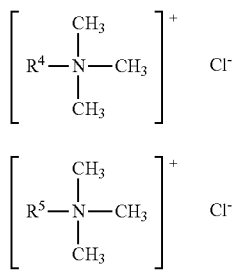

wherein R⁴ represents a $C_{12-16}$ linear chain alkyl group, and R⁵ represents a $C_{18-24}$ linear chain alkyl group.

<12> The cosmetic product for hair bleaching or hair dyeing according to <11> above, wherein R⁴ in the formula (2) preferably contains 14 to 16 carbon atoms.

<13> The cosmetic product for hair bleaching or hair dyeing according to <11> or <12> above, wherein the content of the component (B2) in the second part is preferably 0.01% by mass or more, more preferably 0.02% by mass or more, and even more preferably 0.03% by mass or more, and also, it is preferably 10% by mass or less, more preferably 5% by mass or less, even more preferably 3% by mass or less, further preferably 2% by mass or less, and still further preferably 1% by mass or less.

<14> The cosmetic product for hair bleaching or hair dyeing according to any one of <11> to <13> above, wherein R⁵ in the formula (3) contains preferably 18 to 22 carbon atoms, and more preferably 18 to 20 carbon atoms.

<15> The cosmetic product for hair bleaching or hair dyeing according to any one of <11> to <14> above, wherein the content of the component (B3) in the second part is preferably 0.01% by mass or more, more preferably 0.02% by mass or more, and even more preferably 0.03% by mass or more, and also, it is preferably 10% by mass or less, more preferably 5% by mass or less, even more preferably 3% by mass or less, further preferably 2% by mass or less, and still further preferably 1% by mass or less.

<16> The cosmetic product for hair bleaching or hair dyeing according to any one of <11> to <15> above, wherein the mass ratio of the component (B2) to the component (B3), ((B2)/(B3)), in the second part is preferably 20 to 0.05, more preferably 10 to 0.1, even more preferably 8 to 0.5, and further preferably 5 to 1.

<17> The cosmetic product for hair bleaching or hair dyeing according to any one of <1> to <16> above, wherein the second part further contains the following component (C):

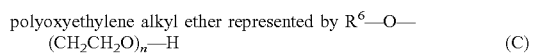

wherein R⁶ represents a $C_{10-24}$ linear or branched chain alkyl group, and n represents the average number of moles added, which is 50 to 210.

<18> The cosmetic product for hair bleaching or hair dyeing according to <17> above, wherein R⁶ in the formula of the component (C) contains preferably 12 to 24 carbon atoms, and more preferably 14 to 22 carbon atoms.

<19> The cosmetic product for hair bleaching or hair dyeing according to <17> or <18> above, wherein n in the formula of the component (C) is preferably 60 or more, more preferably 80 or more, and even more preferably 100 or more, and also it is preferably 200 or less.

<20> The cosmetic product for hair bleaching or hair dyeing according to any one of <17> to <19> above, wherein the content of the component (C) in the second part is preferably 0.01% by mass or more, more preferably 0.03% by mass or more, and even more preferably 0.05% by mass or more, and also it is preferably 15% by mass or less, more preferably 10% by mass or less, even more preferably 5% by mass or less, further preferably 3% by mass or less, still further preferably 2% by mass or less, and still further preferably 1.5% by mass or less.

<21> The cosmetic product for hair bleaching or hair dyeing according to any one of <1> to <20> above, which preferably further contains polyhydric alcohol in an amount of preferably 0.1% by mass or more, more preferably 0.5% by mass or more, and even more preferably 1% by mass or more, and also in an amount of preferably 20% by mass or less, more preferably 15% by mass or less, even more preferably 10% by mass or less, and further preferably 5% by mass or less.

<22> The cosmetic product for hair bleaching or hair dyeing according to any one of <1> to <21> above, wherein the viscosity (5° C.) of the mixture is preferably 1 mPa·s or more, more preferably 2 mPa·s or more, even more preferably 3 mPa·s or more, and further preferably 5 mPa·s or more, and also, it is preferably 800 mPa·s or less, more preferably 500 mPa·s or less, even more preferably 400 mPa·s or less, further preferably 300 mPa·s or less, and still further preferably 200 mPa·s or less.

<23> The cosmetic product for hair bleaching or hair dyeing according to any one of <1> to <22> above, wherein the pH (25° C.) of the mixture is preferably 8 or more, and more preferably 9 or more, and also, it is preferably 12 or less, more preferably 11 or less, and even more preferably 10.5 or less.

<24> Use of the cosmetic product for hair bleaching or hair dyeing according to any one of <1> to <23> above for hair bleaching or hair dyeing.

EXAMPLES

Examples 1 to 16 and Comparative Examples 1 and 2

A first part having the mixing composition shown in Table 1 and second parts shown in Tables 2 to 4 were prepared.

As a non-aerosol foamer container, S1 Squeeze Foamer manufactured by DAIWA CAN COMPANY (volume: 210 mL, mesh roughness in mixing chamber: 150 meshes, mesh roughness at tip; 200 meshes, the total of the opening areas of the narrowest portion of an air introduction pathway: 0.27 mm², the inner diameter of a dip tube: φ1.75 mm) was used.

Immediately after preparation of the second parts and after the long-term preservation of the second parts, the maximum diameter of the emulsified particle and the viscosity of a mixed solution were measured, and also, foam dischargeability under low temperature conditions was evaluated. Moreover, immediately after preparation of the second parts, foam stability under high temperature conditions was evaluated.

The second part within 24 hours after the preparation thereof was defined as a second part immediately after the preparation thereof, whereas the second part after it has been preserved for 6 days in an acceleration test room, in which the temperature has been changed between −15° C. and 60° C. with a period of 24 hours, is defined as a second part after a long-term preservation. These second parts were used in the following evaluation.

(Maximum Diameter of Emulsified Particle Immediately after Preparation of, and after Long-Term Preservation of Second Part)

Employing DYNAMIC LIGHT SCATTERING PARTICLE SIZE ANALYZER LB-500 manufactured by HORIBA, "Organic sample" (refractive index: 1.600-0.000 i) was selected as a sample, and "Water" (refractive index: 1.333) was selected as a dispersion medium. Thereafter, the maximum diameter of the emulsified particle in the second part at 25° C. was read.

(Viscosity of Mixed Solution Under Low Temperature Conditions, Immediately after Preparation of, and after Long-Term Preservation of Second Part)

The first part and the second part was slowly mixed with each other at a mass ratio of 1:2 under conditions of 5° C. in a squeeze foamer container, such that they did not get foamed. Thereafter, the mixture was transferred into Screw Tube No. 8 (manufactured by Maruemu Corporation), and the viscosity of the mixed solution was then measured. As a viscosity (mPa·s) under conditions of 5° C., the value, which was obtained by measuring viscosity using a type-B viscometer and Rotor No. 1 under conditions of 60 rpm (in the case of 100 mPa·s or less) or 30 rpm (in the case of 100 to 200 mPa·s), and then leaving it for 1 minute, was adopted.

(Foam Dischargeability Under Low Temperature Conditions, Immediately after Preparation of, and after Long-Term Preservation of Second Part)

The first part and the second part was slowly mixed with each other at a mass ratio of 1:2 under conditions of 5° C. in a squeeze foamer container, such that they did not get foamed. Subsequently, the dischargeability of the foam was evaluated according the following standards:

4: The foam can be easily discharged with one hand of a general woman.

3: When a general woman tends to discharge the foam with one hand, she feels that it is slightly tight.

2: When a general woman tends to discharge the foam with one hand, she feels that it is tight.

1: A general woman cannot discharge the form with one hand.

(Foam Stability when Foam is Discharged Under High Temperature Conditions, Immediately after Preparation of Second Part)

The first part and the second part was slowly mixed with each other at a mass ratio of 1:2 under conditions of 40° C. in a squeeze foamer container, such that they did not get foamed. Subsequently, 10 g of the foam product was discharged into a beaker, and it was then left at 25° C. for 15 minutes. Thereafter, the liquid amount of a liquid product changed from the foam product (the amount of a liquid discharged) was measured.

TABLE 1

| (% by mass: the contents are all active amounts) | Common first part |
|---|---|
| Alkyl (8-16) glucoside | 2.00 |
| Sodium cocoyl glutamate | 8.10 |
| Laureth-23 | 3.00 |
| (C12-14) s-Pareth-9 | 2.00 |
| Myristyl alcohol | 0.24 |
| Propylene glycol | 4.00 |
| Polypropylene glycol | 1.00 |
| Polyquaternium-22 | 1.10 |
| Strong ammonia water | 1.60 |
| Ammonium hydrogen carbonate | 9.60 |
| Ethanol | 9.50 |
| Tetrasodium edetate dihydrate | q.s. |
| Perfume | q.s. |
| Purified water | Balance |
| Total | 100 |

TABLE 2

| | Second part (% by mass: the contents are all active amounts) | | Example | | | | | |
|---|---|---|---|---|---|---|---|---|
| | | | 1 | 2 | 3 | 4 | 5 | 6 |
| (A1) | Myristyl alcohol | | — | 0.55 | — | — | — | — |
| | Cetyl alcohol | | 0.55 | — | 0.55 | 0.55 | 0.38 | 0.38 |
| | Stearyl alcohol | | — | — | — | — | — | — |
| (A2) | Arachyl alcohol | | — | — | — | — | — | — |
| | Behenyl alcohol | | 0.77 | 0.77 | 0.77 | 0.77 | 0.54 | 0.54 |
| (B) | Cetyltrimethylammonium chloride | | 0.39 | 0.39 | 0.52 | — | — | — |
| | Stearyltrimethylammonium chloride | | 0.13 | 0.13 | — | 0.52 | — | — |
| | Sodium polyoxyethylene (2) lauryl ether sulfate | | — | — | — | — | 0.92 | — |
| | Amidopropylbetaine laurate | | — | — | — | — | — | 0.92 |
| (C) | Ceteth-150 | | 1.0 | 1.0 | 1.0 | 1.0 | 1.0 | 1.0 |
| | Propylene glycol | | 0.5 | 0.5 | 0.5 | 0.5 | 0.5 | 0.5 |
| | Hydrogen peroxide | | 5.70 | 5.70 | 5.70 | 5.70 | 5.70 | 5.70 |
| | Etidronic acid solution | | q.s. | q.s. | q.s. | q.s. | q.s. | q.s. |
| | 8-Quinolinol sulfate | | q.s. | q.s. | q.s. | q.s. | q.s. | q.s. |
| | Sodium hydroxide | | q.s. | q.s. | q.s. | q.s. | q.s. | q.s. |
| | Purified water | | Balance | Balance | Balance | Balance | Balance | Balance |
| | Total | | 100 | 100 | 100 | 100 | 100 | 100 |
| | (A1) + (A2) | | 1.32 | 1.32 | 1.32 | 1.32 | 0.92 | 0.92 |
| | (A1):(A2) | | 5:7 | 5:7 | 5:7 | 5:7 | 5:7 | 5:7 |
| | (B) | | 0.52 | 0.52 | 0.52 | 0.52 | 0.92 | 0.92 |
| | (B)/[(A1) + (A2)] | | 0.4 | 0.4 | 0.4 | 0.4 | 1.0 | 1.0 |
| Evaluation | Maximum diameter of emulsified particle in second part (μm) | Immediately after production of second part | 0.33 | 0.23 | 0.39 | 0.39 | 0.23 | 0.67 |

TABLE 2-continued

| Second part (% by mass: the contents are all active amounts) | | Example | | | | | |
|---|---|---|---|---|---|---|---|
| | | 1 | 2 | 3 | 4 | 5 | 6 |
| | After long-term preservation of second part | 0.51 | 0.34 | 0.51 | 0.51 | 0.58 | 0.20 |
| Increase in maximum diameter of emulsified particle from immediately after production of second part to after long-term preservation of second part (μm) | | +0.18 | +0.11 | +0.12 | +0.12 | +0.35 | −0.47 |
| Viscosity of mixed solution under low temperature conditions (mPa · s) | Immediately after production of second part | 12.3 | 30.4 | 19.8 | 9.5 | 20.9 | 18.3 |
| | After long-term preservation of second part | 16.2 | 38.8 | 28.9 | 14.0 | 18.8 | 5.8 |
| Foam dischargeability under low temperature conditions | Immediately after production of second part | 4 | 4 | 4 | 4 | 4 | 4 |
| | After long-term preservation of second part | 4 | 4 | 4 | 4 | 4 | 4 |
| Amount of liquid discharged under high temperature conditions (g) | Immediately after production of second part | 0 | 0 | 0 | 0 | 0 | 0.77 |

TABLE 3

| | Second part (% by mass: the contents are all active amounts) | | Example | | | | | Comparative Example | |
|---|---|---|---|---|---|---|---|---|---|
| | | | 7 | 8 | 9 | 10 | 11 | 1 | 2 |
| (A1) | Myristyl alcohol | | — | — | — | — | — | — | — |
| | Cetyl alcohol | | 0.33 | 0.16 | 0.66 | 0.88 | 0.99 | 1.32 | — |
| | Stearyl alcohol | | — | — | — | — | — | — | — |
| (A2) | Arachyl alcohol | | — | — | — | — | — | — | — |
| | Behenyl alcohol | | 0.99 | 1.16 | 0.66 | 0.44 | 0.33 | — | 1.32 |
| (B) | Cetyltrimethylammonium chloride | | 0.39 | 0.39 | 0.39 | 0.39 | 0.39 | 0.39 | 0.39 |
| | Stearyltrimethylammonium chloride | | 0.13 | 0.13 | 0.13 | 0.13 | 0.13 | 0.13 | 0.13 |
| | Sodium polyoxyethylene (2) lauryl ether sulfate | | — | — | — | — | — | — | — |
| | Amidopropylbetaine laurate | | — | — | — | — | — | — | — |
| (C) | Ceteth-150 | | 1.0 | 1.0 | 1.0 | 1.0 | 1.0 | 1.0 | 1.0 |
| | Propylene glycol | | 0.5 | 0.5 | 0.5 | 0.5 | 0.5 | 0.5 | 0.5 |
| | Hydrogen peroxide | | 5.7 | 5.7 | 5.7 | 5.7 | 5.7 | 5.70 | 5.70 |
| | Etidronic acid solution | | q.s. | q.s. | q.s. | q.s. | q.s. | q.s. | q.s. |
| | 8-Quinolinol sulfate | | q.s. | q.s. | q.s. | q.s. | q.s. | q.s. | q.s. |
| | Sodium hydroxide | | q.s. | q.s. | q.s. | q.s. | q.s. | q.s. | q.s. |
| | Purified water | | Balance | Balance | Balance | Balance | Balance | Balance | Balance |
| | Total | | 100 | 100 | 100 | 100 | 100 | 100 | 100 |
| | (A1) + (A2) | | 1.32 | 1.32 | 1.32 | 1.32 | 1.32 | 1.32 | 1.32 |
| | (A1):(A2) | | 1:3 | 1:7 | 1:1 | 2:1 | 3:1 | 1:0 | 0:1 |
| | (B) | | 0.52 | 0.52 | 0.52 | 0.52 | 0.52 | 0.52 | 0.52 |
| | (B)/[(A1) + (A2)] | | 0.4 | 0.4 | 0.4 | 0.4 | 0.4 | 0.4 | 0.4 |
| Evaluation | Maximum diameter of emulsified particle in second part (μm) | Immediately after production of second part | 0.45 | 0.39 | 0.30 | 0.34 | 0.34 | 2.60 | 1.15 |
| | | After long-term preservation of second part | 0.67 | 0.51 | 0.51 | 0.67 | 1.15 | 6.00< | 1.73 |
| | Increase in maximum diameter of emulsified particle from immediately after production of second part to after long-term preservation of second part(μm) | | 0.22 | 0.12 | 0.21 | 0.33 | 0.81 | +3.40< | +0.58 |
| | Viscosity of mixed solution under low temperature conditions (mPa · s) | Immediately after production of second part | 15.8 | 24.2 | 11.7 | 20.8 | 23.8 | 62.2 | 8.8 |
| | | After long-term preservation of second part | 14.7 | 14.3 | 23.2 | 25.3 | 29.8 | 177.4 | 10.8 |
| | Foam dischargeability under low temperature conditions | Immediately after production of second part | 4 | 4 | 4 | 4 | 4 | 1 | 4 |

TABLE 3-continued

| Second part (% by mass: the contents are all active amounts) | | Example 7 | Example 8 | Example 9 | Example 10 | Example 11 | Comparative Example 1 | Comparative Example 2 |
|---|---|---|---|---|---|---|---|---|
| | After long-term preservation of second part | 4 | 4 | 4 | 4 | 4 | 1 | 4 |
| Amount of liquid discharged under high temperature conditions (g) | Immediately after production of second part | 0 | 0.74 | 0.23 | 0 | 0.32 | 0 | 3.84 |

TABLE 4

| | Second part (% by mass: the contents are all active amounts) | | Example 12 | Example 13 | Example 14 | Example 15 | Example 16 |
|---|---|---|---|---|---|---|---|
| (A1) | Cetyl alcohol | | 0.38 | 0.5 | 0.59 | 0.64 | 0.55 |
| (A2) | Behenyl alcohol | | 0.54 | 0.7 | 0.83 | 0.9 | 0.77 |
| (B) | Cetyltrimethylammonium chloride | | 0.69 | 0.57 | 0.32 | 0.23 | 0.39 |
| | Stearyltrimethylammonium chloride | | 0.23 | 0.19 | 0.11 | 0.076 | 0.13 |
| (C) | Ceteth-150 | | 1.0 | 1.0 | 1.0 | 1.0 | — |
| | Ceteth-40 | | — | — | — | — | 1.0 |
| | Propylene glycol | | 0.5 | 0.5 | 0.5 | 0.5 | 0.5 |
| | Hydrogen peroxide | | 5.70 | 5.70 | 5.70 | 5.70 | 16.29 |
| | Etidronic acid solution | | q.s. | q.s. | q.s. | q.s. | q.s. |
| | 8-Quinolinol sulfate | | q.s. | q.s. | q.s. | q.s. | q.s. |
| | Sodium hydroxide | | q.s. | q.s. | q.s. | q.s. | q.s. |
| | Purified water | | Balance | Balance | Balance | Balance | Balance |
| | Total | | 100 | 100 | 100 | 100 | 100 |
| | (A1) + (A2) | | 0.92 | 1.2 | 1.42 | 1.54 | 1.32 |
| | (A1):(A2) | | 5:7 | 5:7 | 5:7 | 7:1 | 5:7 |
| | (B) | | 0.92 | 0.76 | 0.43 | 0.31 | 0.52 |
| | (B)/[(A1) + (A2)] | | 1 | 0.63 | 0.3 | 0.2 | 0.4 |
| Evaluation | Maximum diameter of emulsified particle in second part (μm) | Immediately after production of second part | 0.23 | 0.51 | 0.88 | 1.98 | 1.32 |
| | | After long-term preservation of second part | 0.51 | 0.51 | 1.00 | 4.47 | 2.27 |
| | Increase in maximum diameter of emulsified particle from immediately after production of second part to after long-term preservation of second part (μm) | | +0.28 | 0 | +0.12 | +2.49 | +0.95 |
| | Viscosity of mixed solution under low temperature conditions (mPa · s) | Immediately after production of second part | 8.7 | 11 | 19.4 | 40.5 | 26.3 |
| | | After long-term preservation of second part | 11.2 | 15.8 | 27.0 | 58.5 | 77.8 |
| | Foam dischargeability under low temperature conditions | Immediately after production of second part | 4 | 4 | 4 | 4 | 4 |
| | | After long-term preservation of second part | 4 | 4 | 4 | 2 | 3 |
| | Amount of liquid discharged under high temperature conditions (g) | Immediately after production of second part | 0 | 0 | 0 | 0 | 0 |

Example 17

Using the first part with the mixing composition shown in Table 5 and the second part used in Example 1, various evaluations were carried out according to the above described methods and standards. The results are shown in Table 6.

TABLE 5

| (% by mass: the contents are all active amounts) | Common first part |
|---|---|
| Myristic acid | 0.1 |
| Polyquaternium-22 | 1.1 |
| p-Aminophenol | 0.3 |
| m-Aminophenol | 0.4 |
| Resorcin | 1.4 |

TABLE 5-continued

| (% by mass: the contents are all active amounts) | Common first part |
|---|---|
| p-Amino-ortho-cresol | 0.2 |
| Toluene-2,5-diamine | 1.8 |
| Ascorbic acid | 0.4 |
| Anhydrous sodium sulfite | 0.4 |
| Alkyl (8-16) glucoside | 3.2 |
| Sodium cocoyl glutamate | 4.6 |
| Propylene glycol | 2.5 |
| Polypropylene glycol | 2.5 |
| (C12-14) s-Pareth-9 | 4.0 |
| Laureth-23 | 6.0 |
| Myristyl alcohol | 0.4 |
| Monoethanolamine | 2.1 |
| Strong ammonia water | 0.3 |
| Ammonium hydrogen carbonate | 2.5 |
| Sodium hydroxide | 0.3 |
| Ethanol | 9.5 |
| Tetrasodium edetate dihydrate | q.s. |
| Perfume | q.s. |
| Purified water | Balance |
| Total | 100 |

TABLE 6

| | Second part (% by mass: the contents are all active amounts) | | Example 17 |
|---|---|---|---|
| (A1) | Myristyl alcohol | | — |
| | Cetyl alcohol | | 0.55 |
| | Stearyl alcohol | | — |
| (A2) | Arachyl alcohol | | — |
| | Behenyl alcohol | | 0.77 |
| (B) | Cetyltrimethylammonium chloride | | 0.39 |
| | Stearyltrimethylammonium chloride | | 0.13 |
| | Sodium polyoxyethylene (2) lauryl ether sulfate | | — |
| | Amidopropylbetaine laurate | | — |
| (C) | Ceteth-150 | | 1 |
| | Propylene glycol | | 0.5 |
| | Hydrogen peroxide | | 5.7 |
| | Etidronic acid solution | | q.s. |
| | 8-Quinolinol sulfate | | q.s. |
| | Sodium hydroxide | | q.s. |
| | Purified water | | Balance |
| | Total | | 100 |
| | (A1) + (A2) | | 1.32 |
| | (A1):(A2) | | 5:7 |
| | (B) | | 0.52 |
| | (B)/[(A1) + (A2)] | | 0.4 |
| Evaluation | Maximum diameter of emulsified particle in second part (μm) | Immediately after production of second part | 0.33 |
| | | After long-term preservation of second part | 0.51 |
| | Increase in maximum diameter of emulsified particle from immediately after production of second part to after long-term preservation of second part (μm) | | 0.18 |
| | Viscosity of mixed solution under low temperature conditions (mPa · s) | Immediately after production of second part | 30.3 |
| | | After long-term preservation of second part | 30.3 |
| | Foam dischargeability under low temperature conditions | Immediately after production of second part | 4 |
| | | After long-term preservation of second part | 4 |
| | Amount of liquid discharged under high temperature conditions (g) | Immediately after production of second part | 0 |

The invention claimed is:

1. A cosmetic product for hair bleaching or hair dyeing, which comprises
a first part comprising an alkali agent,
a second part comprising hydrogen peroxide and a component (A), and
a non-aerosol foamer container for discharging a mixed solution comprising the first part and the second part in the form of foam,
wherein component (A) is a saturated aliphatic alcohol composition that comprises:

$$a \text{ saturated aliphatic alcohol represented by } R^1\text{—OH} \quad (A1)$$

wherein $R^1$ represents a $C_{12-18}$ linear chain alkyl group, and $$a \text{ saturated aliphatic alcohol represented by } R^2\text{—OH} \quad (A2)$$

wherein $R^2$ represents a $C_{19-24}$ linear chain alkyl group, and
wherein components (A1) and (A2) are present in the second part and a total amount of the combination of components (A1) and (A2) in the second part is from 0.1% by mass to 1.5% by mass,
wherein said second part further comprises (B) an ionic surfactant,
wherein the mass ratio of (A1):(A2) is 3:1 to 1:3, and
wherein the mass ratio of (B)/((A1)+(A2)) is 0.3 to 1.

2. The cosmetic product according to claim 1, wherein a content of component (A1) in the second part is from 0.05% by mass to 1% by mass.

3. The cosmetic product according to claim 1, wherein a content of component (A2) in the second part is from 0.05% by mass to 1% by mass.

4. The cosmetic product according to claim 1, wherein component (B) comprises (B1) a mono-long-chain-alkylammonium salt represented by formula (1):

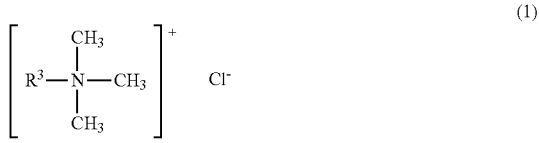

wherein $R^3$ represents a $C_{12-24}$ linear chain alkyl group.

5. The cosmetic product according to claim 4, wherein component (B) comprises:
   (B2) a mono-long-chain-alkylammonium salt represented by formula (2) and
   (B3) a mono-long-chain-alkylammonium salt represented by formula (3):

wherein
$R^4$ represents a $C_{12-16}$ linear chain alkyl group, and
$R^5$ represents a $C_{18-24}$ linear chain alkyl group.

6. The cosmetic product according to claim 5, wherein a mass ratio of component (B2) to component (B3), ((B2)/(B3)), in the second part is from 20 to 0.05.

7. The cosmetic product according to claim 5, wherein a content of component (B2) in the second part is from 0.01% to 10% by mass.

8. The cosmetic product according to claim 5, wherein a content of component (B3) in the second part is from 0.01% by mass to 10% by mass.

9. The cosmetic product according to claim 1, wherein the second part further comprises component (C):
   (C) a polyoxyethylene alkyl ether represented by $R^6$—O—$(CH_2CH_2O)_n$—H wherein $R^6$ represents a $C_{10-24}$ linear or branched chain alkyl group, and n represents the average number of moles added, which is 50 to 210.

10. The cosmetic product according to claim 9, wherein a content of component (C) in the second part is from 0.01% by mass to 15% by mass.

11. The cosmetic product according claim 1, wherein the viscosity (5° C.) of the mixed solution is from 1 mPa·s to 800 mPa·s.

12. A method for bleaching or dyeing hair, comprising:
    contacting hair with the mixed solution from the cosmetic product according claim 1, and
    removing the mixed solution from said hair after said contacting.

13. The cosmetic product according to claim 1, wherein a total amount of the combination of components (A1) and (A2) in the second part is from 0.1% by mass to 1.42% by mass.

14. The cosmetic product according to claim 1, wherein a total amount of the combination of components (A1) and (A2) in the second part is from 0.92% by mass to 1.42% by mass.

15. The cosmetic product according to claim 1, wherein component (A1) is cetyl alcohol and component (A2) is behenyl alcohol.

16. The cosmetic product according to claim 1, wherein component (A1) is cetyl alcohol and component (A2) is behenyl alcohol and a total amount of the combination of components (A1) and (A2) in the second part is from 0.1% by mass to 1.42% by mass.

17. The cosmetic product according to claim 1, wherein component (A1) is cetyl alcohol and component (A2) is behenyl alcohol and a total amount of the combination of components (A1) and (A2) in the second part is from 0.92% by mass to 1.42% by mass.

* * * * *